US00PP12987P2

(12) United States Plant Patent
Olesen et al.

(10) Patent No.: US PP12,987 P2
(45) Date of Patent: Sep. 17, 2002

(54) ROSE PLANT NAMED 'POULSHRIMP'

(76) Inventors: L. Pernille Olesen; Mogens N. Olesen, both of Hilerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/780,136

(22) Filed: Feb. 8, 2001

(51) Int. Cl.[7] ..... A01H 5/00
(52) U.S. Cl. ..... Plt./122
(58) Field of Search ..... Plt./122

(56) References Cited

PUBLICATIONS

UPOV–ROM GTITM Computer Database, 2001/04, GTI Jouve Retrieval Software, citaton for 'POULshrimp'.*

* cited by examiner

*Primary Examiner*—Bruce R. Campell
*Assistant Examiner*—Susan B. McCormick

(57) ABSTRACT

A new miniature rose which has abundant, orange-red flowers and attractive foliage. This new and distinct variety has shown to be uniform and stable in the resulting generations from asexual propagation.

1 Drawing Sheet

BOTANICAL CLASSIFICATION

*Rosa hybrida.*

VARIETY DENOMINATION

'POULshrimp'.

SUMMARY OF THE INVENTION

The present invention constitutes a new and distinct variety of miniature rose plant which originated from a controlled crossing between 'POULege', a rose by the same inventors, described and illustrated in U.S. Plant patent application Ser. No. 09/282,073 dated Mar. 29, 1999; and 'POULvic', a rose by the same inventors, described and illustrated in U.S. Plant Pat. No. 8,012 issued on Oct. 27, 1994. The two parents were crossed during the summer of 1990 and the resulting seeds were planted in a controlled environment in Fredensborg, Denmark. The new variety is named 'POULshrimp'.

The new rose may be distinguished from its seed parent, 'POULege', by the following combination of characteristics:

1. 'POULshrimp' has bright orange-red blooms, whereas the 'POULege' has salmon-orange blooms.
2. 'POULshrimp' is a miniature garden rose, whereas 'POULege' is a floribunda rose.
3. 'POULshrimp' exhibits more compact and even and growth than 'POULege'.

The new variety may be distinguished from its pollen parent, 'POULvic' by the following combination of characteristics:

1. 'POULshrimp' has bright orange-red blooms, whereas 'POULvic' has red blooms.
2. 'POULshrimp' exhibits less flowers per stem when compared to 'POULvic'.
3. 'POULshrimp' is a larger plant in height and width than 'POULvic'.

The objective of the hybridization of this rose variety was to create a new and distinct variety for garden use with unique qualities, such as:

1. Uniform and abundant flowers;
2. Vigorous, but compact growth;
3. Disease resistance.

This combination of qualities is not present in previously available commercial cultivars of this type and distinguish 'POULshrimp' from all other varieties of which we are aware.

As part of their rose development program, L. Pernille Olesen and Mogens N. Olesen germinated the seeds from the aforementioned hybridization during winter 1990 and conducted evaluations on the resulting seedlings in a controlled environment in Fredensborg, Denmark.

'POULshrimp' was selected in the spring of 1991 by the inventors as a single plant from the progeny of the aforementioned hybridization.

Asexual reproduction of 'POULshrimp' by traditional budding and rooted cuttings was first done by L. Pernille and Mogens N. Olesen in their nursery in Fredensborg, Denmark in summer 1991. This initial and other subsequent asexual propagations conducted in controlled environments have demonstrated that the characteristics of 'POULshrimp' are true to type and are transmitted from one generation to the next.

BRIEF DESCRIPTION OF THE DRAWING

The accompanying color illustration shows as true as is reasonably possible to obtain in color photographs of this type the variety rose 'POULshrimp'. Specifically illustrated in SHEET 1 include 'POULshrimp's' foliage, flower buds, partially opened buds, and numerous open blooms.

DETAILED DESCRIPTION OF THE VARIETY

The following is a description of 'POULshrimp', as observed in its Half Moon Bay, Calif. Oregon, on plants aged sixteen weeks. Root development for the observed plant typically takes 8 to 10 weeks. Color references are made using The Royal Horticultural Society (London, England) Colour Chart, 1995, except where common terms of color are used. For a comparison, several physical characteristics of the rose variety 'POULrouge', a rose variety from the same inventors described and illustrated in U.S. Plant Pat. No. 9,687 issued on Nov. 12, 1996 are compared to 'POULshrimp' in Chart 1.

CHART 1

| | 'POULshrimp' | 'POULrouge' |
|---|---|---|
| Color of open flower, inner side, middle zone. | Red Group 45C | Red Group 40B |
| Petalage | 25–30 | 30–35 |
| Upon opening, color basal petal spot, outer side | Yellow Group 5C | Yellow Group 7D |

Parents:

*Seed parent.*—'POULege'.

*Pollen parent.*—'POULvic'.

FLOWER AND FLOWER BUD

Blooming habit: Nearly continuous.

Flower bud:

*Bud size.*—Upon opening, 20 mm in length from bas of receptacle to end of bud.

*Color.*—As sepals unfold, Red Group 43C; Red Group 43B at ¼ opening.

*Diameter* 35–40 mm.

*Bud form.*—Broad ovate.

*Sepals.*—Strong foliaceous appendages on 3 of the 5 sepals. Surfaces of sepals are slightly pubescent. Numerous stipitate glands present on sepal margins and undersides. Color: Upper surface is Yellow-Green Group 146A at margins and Yellow-Green Group 146D in interior. Size: 20–24 mm long and 5–7 mm wide.

*Receptacle.*—Size: 3 mm high and 3 mm wide. Color: Yellow-Green Group 146C. Surface: With sparse, fine white hairs.

*Peduncle.*—Surface: Above average abundance of hairs and prickles. Length: 40 to 45 mm. Color: Yellow-Green Group 146D. Strength: Strong.

*Borne.*—Large tufts with 3–25 flowers per stem.

Flower bloom:

*Fragrance.*—Little to none.

*Size.*—Small. Average flower diameter is 50–60 mm when open.

*Form.*—Shape of flower when viewed from the side: Upper part: Flattened convex. Lower part: Flat. Viewed from above: Star-shaped.

*Petalage.*—Double. Average range: 20–30 petals under normal conditions.

Color:

*Upon opening, petals.*— Outermost petals: Upper Surface: Red Group 43B. Reverse Side: Red Group 46C. Innermost petals: Upper Surface: Red Group 43A. Reverse Side: Red Group 46D.

*Upon opening, basal petal spots.*—Outermost petals: Outer Side: Yellow Group 1C. Inner Side: Yellow Group 1B. Innermost petals: Outer Side: Yellow Group 1C. Inner Side: Yellow Group 1B.

*After opening, petals.*—Outermost petals: Upper Surface: Red Group 43B/C. Reverse Side: Red Group 47C. Innermost petals: Upper Surface: Red Group 43B. Reverse Side: Red Group 46D.

*Upon opening, basal petal spots.*—Outermost petals: Inner Side: Yellow Group 1B. Innermost petals: Outer Side: Yellow Group 1B. Inner Side: Yellow Group 1B.

General tonality: On open flower Red Group 43B.

Petals:

*Petal reflex.*—Outer petals are double reflex.

*Petal edge.*—Entire, with very small point in center of margin.

*Shape.*—Obovate.

*Petaloids.*—Present; from 5 to 7 under normal conditions.

*Thickness.*—Average.

*Arrangement.*—Not formal.

*Size.*—Petals are 15 mm long and 10–12 mm wide.

Reproductive organs:

*Pollen.*—None noted.

*Pistils.*—Length: 12–13 mm long. Quantity: 35.

*Anthers.*—Size: 1 to 2 mm long. Color: Orange Group 26B at margins; Red Group 39B in interior. Quantity: 45.

*Filaments.*—Color: Yellow Group 5A. Length: 1 to 3 mm.

*Stigmas.*—Superior relative to anthers. Color: Yellow-Green Group 145D.

*Styles.*—Color: Yellow-Green Group 145C–D, with intonations of Red Group 50B.

PLANT

Plant growth: Dense, bushy, compact, low, and even in growth. When grown as a budded field grown plant on *Rosa multiflora* understock, the average height of the plant is 40–50 cm and the average width is 40 cm.

Stems:

*Thorns.*—Incidence: Few. Size: 5 to 8 mm long. Shape: Concave to flat. Color: Yellow-Green Group 144A. Length: Stem length is typically 20 to 25 cm. Diameter: Stem diameter is typically 4 to 6 mm.

Plant foliage:

*Leaf size.*—75–85 mm long and 54–50 mm wide.

*Glossiness.*—Leaflets are faintly glossy.

*Color.*—Upper Leaflet Surface: Green Group 137A. Lower Leaflet Surface: Green Group 138B. Juvenile foliage: Exhibits anthocyanin on young shoots. Anthocyanin intonation: Color: Greyed-Red Group 178A.

Plant leaflets:

*Leaflet.*—Cross Section: Flat. Margin Undulation: Absent to very weak.

*Terminal leaflet.*—Length of blade: 35–40 mm long. Width of blade: 25–30 mm wide. Shape: Ovate.

Disease resistance: Above average resistance to mildew, rust, black spot, and Botrytis under normal growing conditions in Fredensborg, Denmark and Hannover, Germany.

Cold Hardiness: The variety 'POULshrimp' has been found to be resistant to damage from cold, heat and drought damage in USDA Zone 7.

We claim:

1. A new and distinct variety of rose plant of the miniature rose class, substantially as herein illustrated and described as a distinct and novel rose variety due to its abundant orange-red flowers, disease resistance, and extended period of bloom.

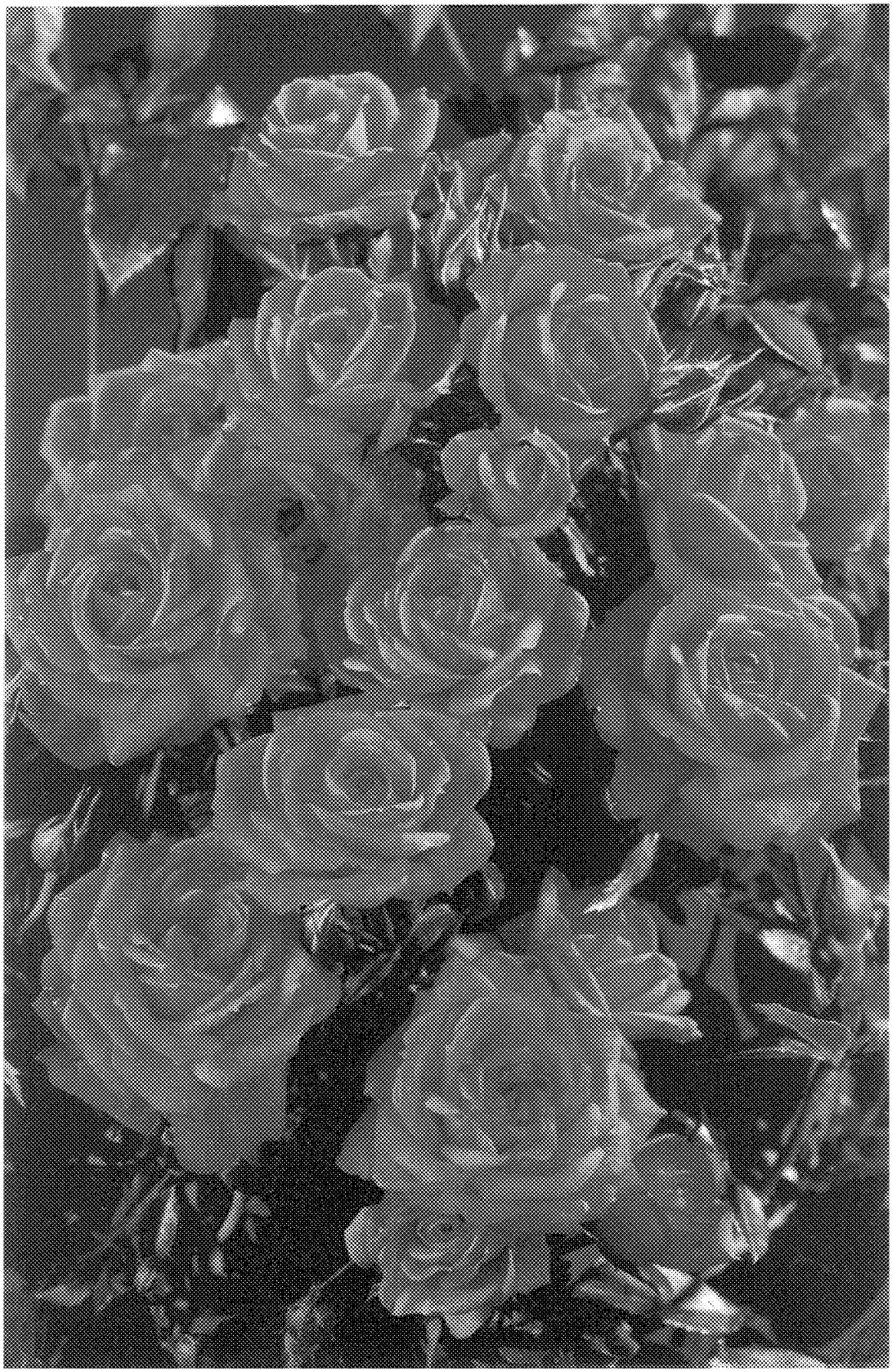

* * * * *